US007641858B2

United States Patent
Kim et al.

(10) Patent No.: US 7,641,858 B2
(45) Date of Patent: Jan. 5, 2010

(54) APPARATUS FOR INTRODUCING FLUID INTO MICROFLUIDIC CHIP BY USING CENTRIFUGAL FORCE, A SYSTEM INCLUDING THE APPARATUS, AND A METHOD OF USING THE APPARATUS

(75) Inventors: Young-rok Kim, Yongin-si (KR); Jun-hong Min, Yongin-si (KR); Kak Namkoong, Yongin-si (KR); Kwang-ho Cheong, Yongin-si (KR); Chang-eun Yoo, Yongin-si (KR); Ki-woong Han, Yongin-si (KR); Ki-eun Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 27 days.

(21) Appl. No.: 11/846,794

(22) Filed: Aug. 29, 2007

(65) Prior Publication Data

US 2008/0072994 A1    Mar. 27, 2008

(30) Foreign Application Priority Data

Sep. 26, 2006  (KR)  .................. 10-2006-0093681

(51) Int. Cl.
  *B01L 3/14*  (2006.01)
  *B65B 3/04*  (2006.01)
(52) U.S. Cl. ............................. 422/99; 422/918; 141/1; 141/34
(58) Field of Classification Search .................. 141/5, 141/34; 210/360.1, 360.2, 361, 512.1, 512.2, 210/512.3, 787–789; 137/825; 422/99, 100, 422/102, 918
See application file for complete search history.

(56) References Cited

U.S. PATENT DOCUMENTS 4,940,527 A    7/1990   Kazlauskas et al.

(Continued)

FOREIGN PATENT DOCUMENTS

DE     198 54 096 A1    5/2000

(Continued)

OTHER PUBLICATIONS

European Search Report for Application No. 07116955.1-2113; Date of Mailing: Jan. 30, 2008 (All references cited in Search Report are cited above).

*Primary Examiner*—Timothy L Maust
*Assistant Examiner*—Nicolas A Arnett
(74) *Attorney, Agent, or Firm*—Cantor Colburn LLP

(57) ABSTRACT

An apparatus introducing a fluid using a centrifugal force includes an introduction member including a chip receiver and a fluid introduction reservoir, the chip receiver receiving a first part of a microfluidic chip, the first part including an inlet, the fluid introduction reservoir storing a fluid to be introduced to the microfluidic chip, the fluid introduction reservoir having an exit formed to correspond to the inlet of the microfluidic chip received in the chip receiver, and a support member supporting a second part of the microfluidic chip, wherein the microfluidic chip is disposed between the introduction member and the support member, the apparatus is rotatable in a state where the introduction member is closer to a center of rotation than the microfluidic chip, and the fluid is introducible from the fluid introduction reservoir through the inlet into the microfluidic chip due to a centrifugal force generated by rotation.

20 Claims, 8 Drawing Sheets

U.S. PATENT DOCUMENTS

| | | | |
|---|---|---|---|
| 6,123,119 A * | 9/2000 | Okumura | 141/34 |
| 6,743,632 B2 * | 6/2004 | Clarke et al. | 436/45 |
| 6,881,315 B2 * | 4/2005 | Iida et al. | 204/600 |
| 7,586,091 B2 * | 9/2009 | Takahashi et al. | 250/288 |
| 2003/0044322 A1 * | 3/2003 | Andersson et al. | 422/100 |
| 2004/0120856 A1 * | 6/2004 | Andersson et al. | 422/72 |
| 2004/0197233 A1 * | 10/2004 | Nagaoka et al. | 422/81 |
| 2006/0073075 A1 * | 4/2006 | Nagaoka et al. | 422/64 |
| 2006/0160688 A1 * | 7/2006 | Namkoong et al. | 494/16 |
| 2006/0185584 A1 * | 8/2006 | Kim et al. | 117/200 |

FOREIGN PATENT DOCUMENTS

| | | |
|---|---|---|
| EP | 1 464 398 A | 10/2004 |
| EP | 1 645 882 A1 | 4/2006 |
| WO | 00/31422 | 6/2000 |

* cited by examiner

CENTRIFUGAL FORCE

CENTER OF ROTATION

APPARATUS FOR INTRODUCING FLUID INTO MICROFLUIDIC CHIP BY USING CENTRIFUGAL FORCE, A SYSTEM INCLUDING THE APPARATUS, AND A METHOD OF USING THE APPARATUS

This application claims priority to Korean Patent Application No. 10-2006-0093681, filed on Sep. 26, 2006, and all the benefits accruing therefrom under 35 U.S.C. §119, the contents of which in its entirety are herein incorporated by reference.

BACKGROUND OF THE INVENTION

1. Field of the Invention

The present invention relates to an apparatus for introducing a fluid into a microfluidic device, a system including the apparatus, and a method of using the apparatus, and more particularly, to an apparatus for introducing a fluid, such as a sample, into the microfluidic device using pressure on the fluid, a system including the apparatus and a rotating device, and a method of using the apparatus.

2. Description of the Related Art

In general, a biochip refers to a microfluidic device including a collection of microfluidic structures fabricated on a chip-shaped substrate to conduct tests including biochemical reactions in the microfluidic device. A driving pressure is necessary to provide a fluid into the microfluidic device, i.e., the biochip. External pumping means, such as a syringe pump or a vacuum pump, is used to provide such a driving pressure.

To satisfy the conditions upon which the microfluidic device can function correctly, the driving pressure should be properly controlled when the fluid, such as a sample or a buffer, is introduced. As microfluidic devices become more complex, it is becoming more important to properly control such a driving pressure. Accordingly, fluid introduction into the complex microfluidic devices requires more time and effort, and may require relatively complex auxiliary equipment.

BRIEF SUMMARY OF THE INVENTION

The present invention provides an apparatus for introducing a fluid to a microfluidic device at an appropriate driving pressure using a centrifugal force provided by a simple device.

The present invention also provides a system including the apparatus for introducing a fluid to a microfluidic device and a rotating device for generating the centrifugal force.

The present invention also provides a method of using the apparatus for introducing a fluid to a microfluidic device by using a rotating device, such as a centrifuge, to generate a centrifugal force to introduce the fluid to a microfluidic device.

According to exemplary embodiments of the present invention, an apparatus introducing a fluid using a centrifugal force includes an introduction member including a chip receiver and a fluid introduction reservoir, the chip receiver receiving a first part of a microfluidic chip, the first part including an inlet, the fluid introduction reservoir storing a fluid to be introduced to the microfluidic chip, the fluid introduction reservoir having an exit formed to correspond to the inlet of the microfluidic chip received in the chip receiver, and a support member supporting a second part of the microfluidic chip, wherein the microfluidic chip is disposed between the introduction member and the support member, the apparatus is rotatable in a state where the introduction member is closer to a center of rotation than the microfluidic chip, and the fluid is introducible from the fluid introduction reservoir through the inlet into the microfluidic chip due to a centrifugal force generated by rotation.

The support member further may include a discharged fluid reservoir receiving a fluid discharged from an outlet of the microfluidic chip. The support member may be a tube-shaped container including a support which may support the microfluidic chip, and at least a portion of the introduction member may be disposed within the tube-shaped container. The support member may be shaped to be received by a centrifuge.

The outer surface of the chip receiver may be attached to at least a portion of an outer surface of the microfluidic chip around the inlet of the microfluidic chip to prevent leakage of the fluid.

According to other exemplary embodiments of the present invention, a system for introducing a fluid by using a centrifugal force includes an introduction member including a chip receiver and a fluid introduction reservoir, the chip receiver receiving a first part of a microfluidic chip, the first part including an inlet, the fluid introduction reservoir storing a fluid to be introduced to the microfluidic chip, the fluid introduction reservoir having an exit formed to correspond to the inlet of the microfluidic chip received in the chip receiver, a support member supporting a second part of the microfluidic chip, the microfluidic chip disposed between the support member and the introduction member, and a rotating device capable of rotating the support member and the introduction member in a state where the introduction member is closer to a center of rotation than the microfluidic chip to introduce the fluid from the fluid introduction reservoir through the inlet into the microfluidic chip due to a centrifugal force generated by rotation.

The support member further may include a discharged fluid reservoir receiving a fluid discharged from an outlet of the microfluidic chip. The support member may be a tube-shaped container having therein a support which may support the microfluidic chip, and at least a portion of the introduction member may be disposed within the tube-shaped container. The rotating device may be a centrifuge, and the support member may be shaped to be received by the centrifuge.

The outer surface of the chip receiver may be attached to at least a portion of an outer surface of the microfluidic chip around the inlet of the microfluidic chip to prevent leakage of the fluid.

According to still other exemplary embodiments of the present invention, there is provided a method of introducing a fluid into a microfluidic chip, the method including preparing a fluid introduction apparatus, the apparatus including an introduction member including a chip receiver and a fluid introduction reservoir, the chip receiver receiving a first part of a microfluidic chip, the first part including an inlet, the fluid introduction reservoir having an exit formed to correspond to the inlet of the microfluidic chip received in the chip receiver, and a support member of the fluid introduction apparatus supporting a second part of the microfluidic chip, disposing the microfluidic chip in the fluid introduction apparatus between the introduction member and the support member, filling the fluid introduction reservoir with a fluid, and rotating the fluid introduction apparatus in which the microfluidic device is disposed by arranging the introduction member to be closer to a center of rotation than the microfluidic chip, and introducing the fluid from the fluid introduction reservoir into the microfluidic chip.

The exemplary embodiment may further include repeating preparing the fluid introduction apparatus, filling the introduction reservoir with the fluid, and rotating the fluid introduction apparatus according to a type of fluid introduced into the microfluidic chip. That is, contamination caused during the fluid introduction process can be prevented by using a new fluid introduction apparatus for each fluid.

According to yet other exemplary embodiments of the present invention, an apparatus for introducing a fluid into a microfluidic device by using a centrifugal force, includes an introduction member including a chip receiver and a fluid introduction reservoir, the chip receiver configured to receive a first part of a microfluidic device, the fluid introduction reservoir configured to store a fluid, the fluid introduction reservoir having an exit leading to the chip receiver, and a support member configured to support a second part of a microfluidic chip, the support member shaped to be received by a rotating device.

The apparatus may further include a microfluidic device having a first part received in the chip receiver and a second part supported by the support member, the first part having an inlet, wherein the inlet of the microfluidic device is in fluid communication with the exit of the fluid introduction reservoir, and fluid from the fluid introduction reservoir is introducible into the microfluidic device using a centrifugal force generated by rotation of the apparatus.

BRIEF DESCRIPTION OF THE DRAWINGS

The above and other aspects, features and advantages of the present invention will become more apparent by describing in more detail exemplary embodiments thereof with reference to the accompanying drawings in which.

DETAILED DESCRIPTION OF THE INVENTION

Figure 1A:
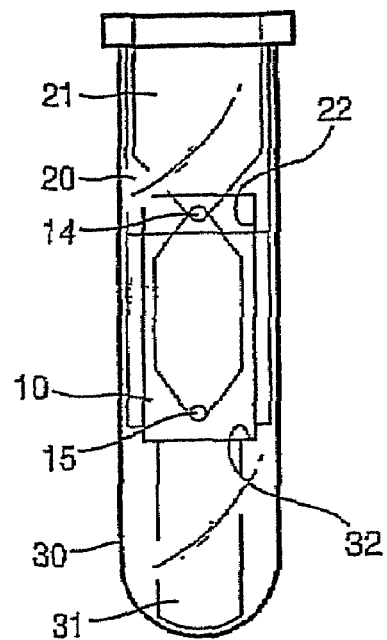
FIG. 1A is a front view of an exemplary fluid introduction apparatus according to an exemplary embodiment of the present invention.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as; "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

The present invention will now be described in detail with reference to the accompanying drawings.

Figure 1B:
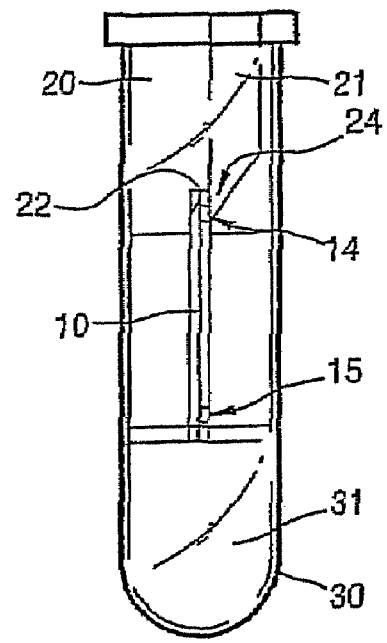
FIG. 1B is a side view of an exemplary fluid introduction apparatus according to an exemplary embodiment of the present invention.

FIG. 1A is a front view of an exemplary fluid introduction apparatus according to an exemplary embodiment of the present invention. FIG. 1B is a side view of the exemplary fluid introduction apparatus according to the present invention.

Referring to FIGS. 1A and 1B, the exemplary fluid introduction apparatus includes an introduction member 20 including a fluid introduction reservoir 21, a microfluidic chip 10, a chip receiver 22 and a support member 30. The fluid introduction reservoir 21 includes an exit 24. The fluid introduction reservoir 21 stores a fluid 25 that is to be introduced to a microfluidic chip 10. The chip receiver 22 receives a part of the microfluidic chip 10 including an inlet 14. The support member 30 includes a support 32 which supports another part of the microfluidic chip 10.

The exit 24 of the fluid introduction reservoir 21 is formed in the chip receiver 22. The exit 24 of the chip receiver 22 corresponds to the position of the inlet 14 of the microfluidic chip 10 that is received by the chip receiver 22. The circumference of the exit 24 corresponds to the circumference of the inlet 14 of the microfluidic chip 10. In one exemplary embodiment, when the introduction member 20 is formed of a flexible material, the chip receiver 22 may be slightly thinner than the microfluidic chip 10 such that the exit 24 and the inlet 14, through which a fluid 25 passes, are sealed. In exemplary embodiments, the number and positions of exits 24 may be varied according to the number and positions of inlets 14 of the microfluidic chip 10. In further exemplary embodiments, the chip receiver 22 may be a slit formed in a side of the introduction member 20. However, the present invention is not limited thereto, and the chip receiver 22 may have any shape to allow it to receive a part of the microfluidic chip 10 including the inlet 14 and to include the exit 24 which corresponds to the circumference of the inlet 14 as described above.

Figure 4:
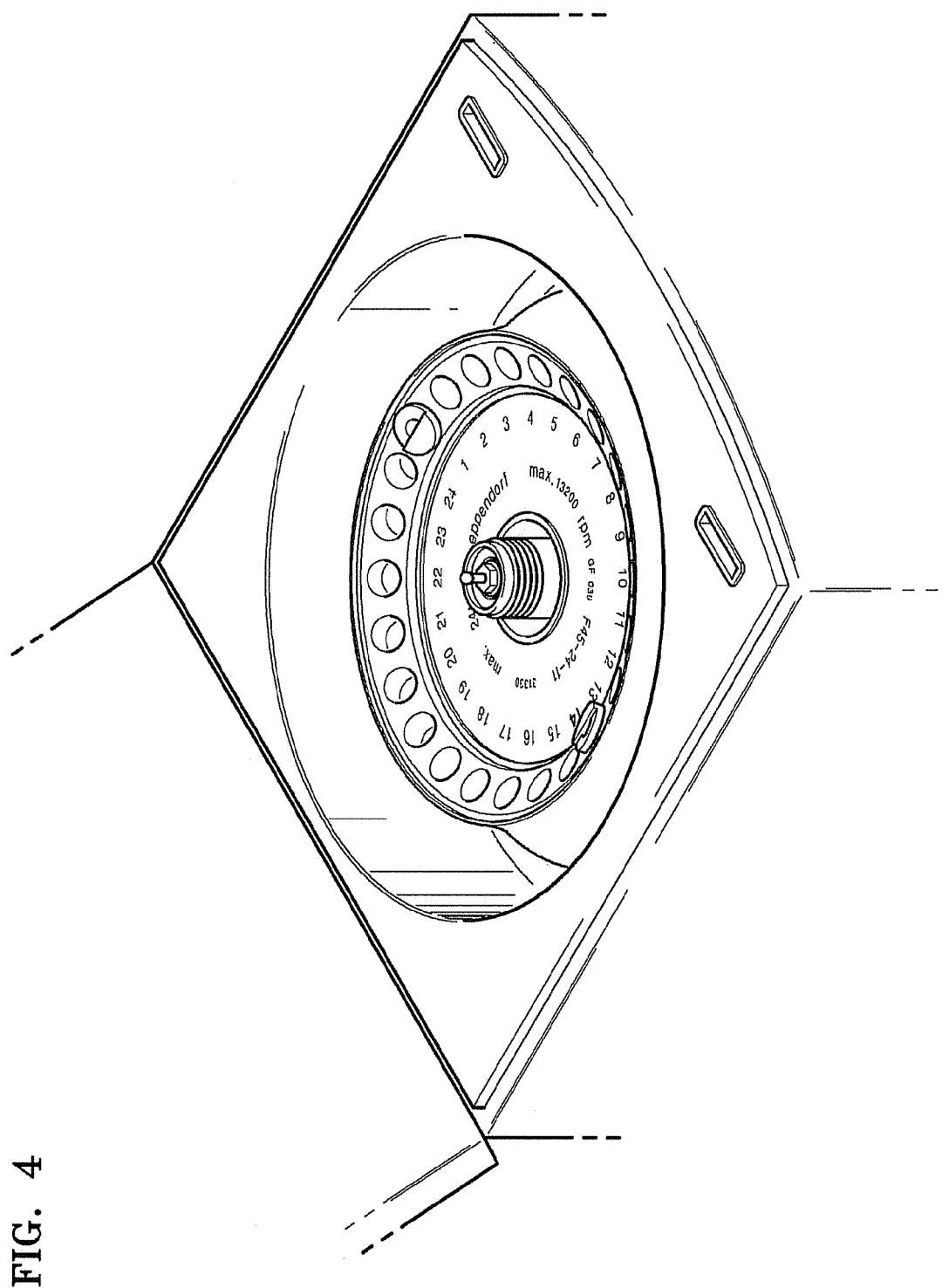
FIG. 4 is a view of an exemplary rotating device which receives the exemplary fluid introduction apparatus of FIGS. 1A and 1B.

The support member 30 includes the support 32 that can support or substantially hold another part of the microfluidic chip 10 that is partially received in the introduction member 20, that is, a part of the microfluidic chip 10 other than the part of the microfluidic chip 10 including the inlet 14. The support member 30 supports or substantially holds the introduction member 20 together with the microfluidic chip 10 to prevent the microfluidic chip 10 from being separated from the chip receiver 22 due to a centrifugal force generated during rotation of the fluid introduction apparatus, and also to prevent an excessive load from being applied to the microfluidic chip 10. In an exemplary embodiment, the support member 30 may be a container that receives and supports at least a part of the introduction member 20 and the microfluidic chip 10. In one exemplary embodiment, the support member 30 may be a tube-shaped container that can be mounted on, or otherwise received by, a rotating device such as shown in FIG. 4, such as a centrifuge. However, the shape of the support member 30 of the present invention is not limited thereto. In an exemplary embodiment a centrifuge and/or a rotating device includes, but is not limited to, substantially tube-shaped openings, e.g., circular and/or cylindrical openings, as shown in FIG. 4, which can receive a tube-shaped support member.

The microfluidic chip 10 includes an outlet 15 formed on a different end to that of the inlet 14, such that the fluid 25 can flow from the inlet 14 to the outlet 15. In this case, the support member 30 may include a discharged fluid reservoir 31 which receives a fluid 25 discharged from the outlet 15.

Figure 2A:
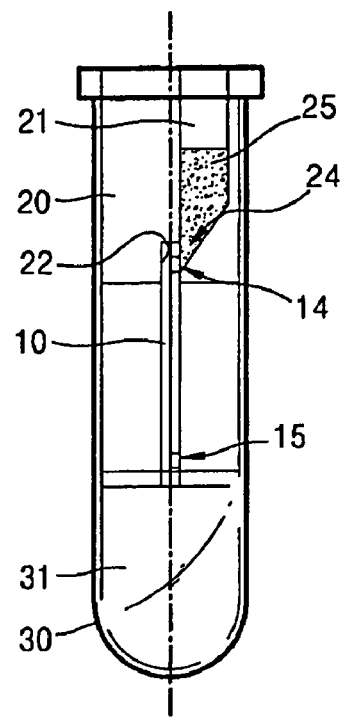
FIG. 2A is a side view of the exemplary fluid introduction apparatus of FIGS. 1A and 1B illustrating a fluid being introduced to a microfluidic chip according to an exemplary embodiment of the present invention.
Figure 2B:
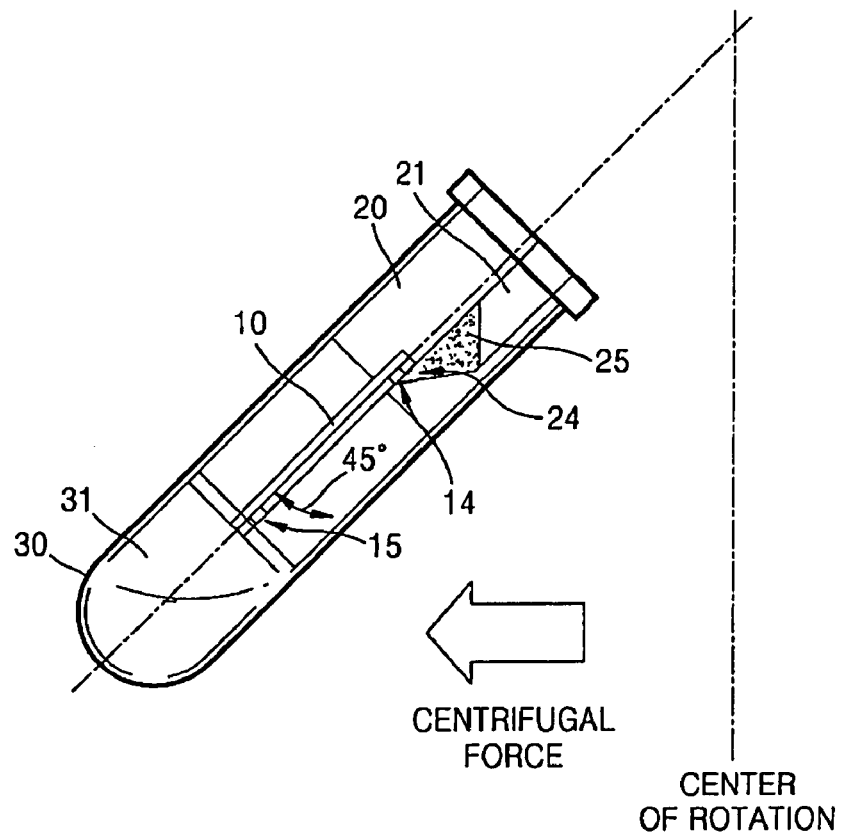
FIG. 2B is a side view of the exemplary fluid introduction apparatus of FIGS. 1A and 1B illustrating a fluid being subjected to a centrifugal force according to an exemplary embodiment of the present invention.

FIG. 2A is a side view of the exemplary fluid introduction apparatus of FIGS. 1A and 1B illustrating a fluid being introduced to a microfluidic chip according to an exemplary embodiment of the present invention. FIG. 2B is a side view of the exemplary fluid introduction apparatus of FIGS. 1A and 1B illustrating a fluid being subjected to a centrifugal force according to an exemplary embodiment of the present invention.

A method of introducing a fluid 25 to the microfluidic chip 10 using the exemplary fluid introduction apparatus of FIGS. 1A and 1B will now be explained with reference to FIGS. 2A and 2B. Referring to FIG. 2A, the microfluidic chip 10 is mounted between the chip receiver 22 of the introduction member 20 and the support 32 of the support member 30, and a fluid 25 is filled in the fluid introduction reservoir 21 of the introduction member 20. Next, referring to FIG. 2B, the exemplary fluid introduction apparatus is mounted on a rotating device such as the rotating device shown in FIG. 4, e.g., a centrifuge, and the centrifuge rotates the fluid introduction apparatus while the introduction member 20 is arranged closer to a center of rotation than the microfluidic chip 10.

When a centrifugal force is generated in a direction marked by an arrow as shown in FIG. 2B and the pressure of the fluid 25 at the exit 24 of the fluid introduction reservoir 21 is increased by the centrifugal force, the fluid 25 is transferred to the inlet 14 of the microfluidic chip 10 due to the centrifugal pressure. At this time, a flow rate can be controlled by the rotation speed of the rotating device, e.g., the centrifuge.

The fluid 25 is not limited in any respect in the current exemplary embodiment. In exemplary embodiments, the fluid 25 may be a biological sample, a reagent necessary for a certain reaction, or a buffer solution for washing or dilution.

Exemplary embodiments of the biological sample may include saliva, sputum, blood, blood cells (such as, leukocytes and erythrocytes), amniotic fluid, serum, semen, bone marrow, urine, a peritoneal fluid, a pleural fluid, cell cultures and a combination of thereof biological samples. In another exemplary embodiment, when a variety of fluids are sequentially introduced into one microfluidic chip 10, a different introduction member 20 should be used for each fluid to prevent contamination that could be caused during the fluid introduction process.

Figure 3:
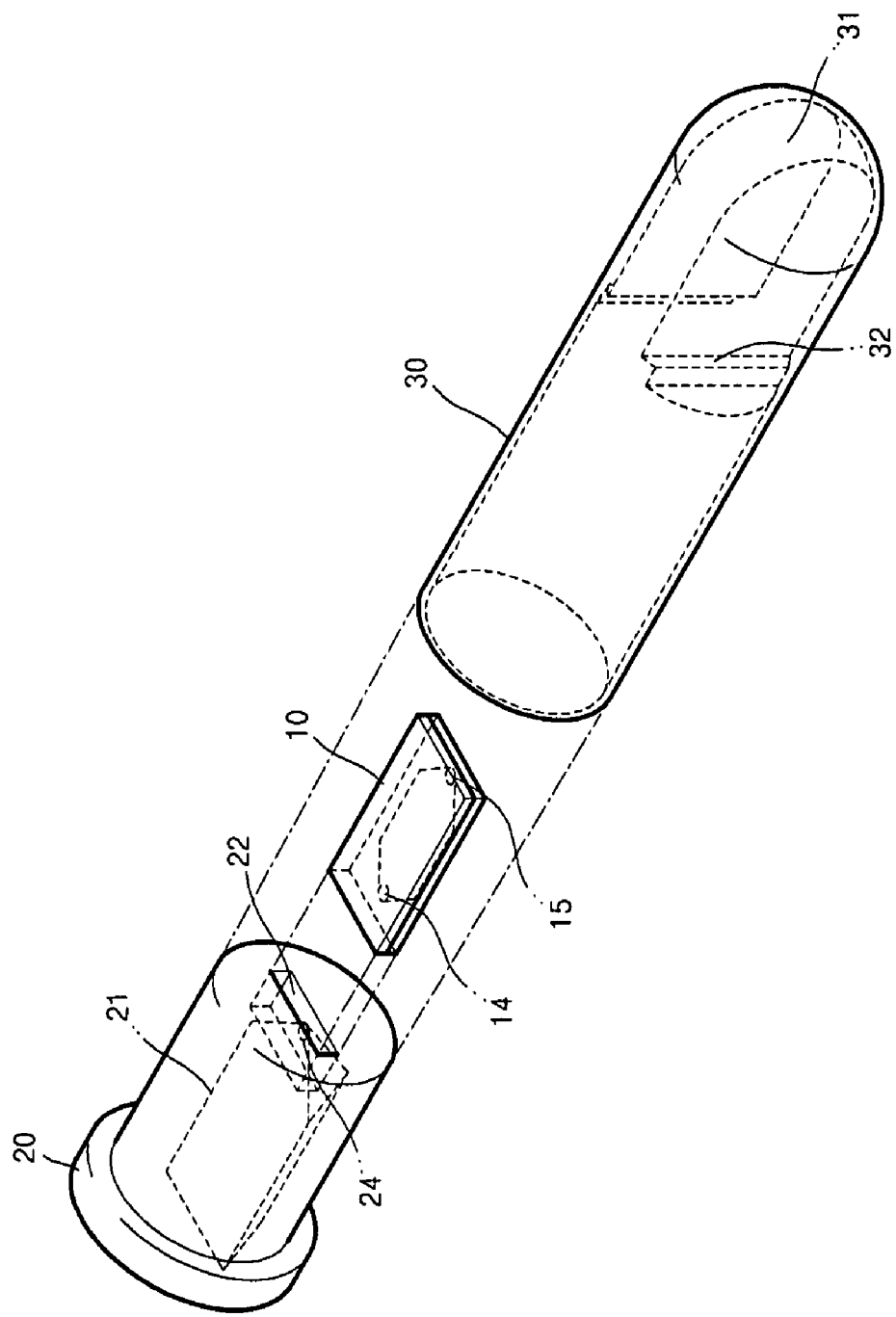
FIG. 3 is an exploded perspective view of the exemplary fluid introduction apparatus of FIGS. 1A and 1B according to an exemplary embodiment of the present invention.

FIG. 3 is an exploded perspective view of the exemplary fluid introduction apparatus of FIGS. 1A and 1B, illustrating the exemplary fluid introduction apparatus separated from the microfluidic chip 10 into which a fluid 25 is to be introduced. The respective elements of FIG. 3 are the same as those described above in FIGS. 1A and 1B. FIG. 4 is a view of an exemplary rotating device which receives the exemplary fluid introduction apparatus of FIGS. 1A and 1B.

In exemplary embodiments, the microfluidic chip 10 includes a collection of microfluidic structures, such as chambers and channels, fabricated on a chip-shaped substrate. The microfluidic chip 10 includes the inlet 14 and the outlet 15. The inlet 14 permits a fluid, such as a sample, to be introduced therein, and the outlet 15 permits the introduced fluid or an aqueous or gaseous fluid residing in the microfluidic chip 10 to be discharged thereout.

The rotating device as shown in FIG. 4 may be capable of rotating the support member 30 and the introduction member 20 in a state where the introduction member 20 is closer to a center of rotation than the microfluidic chip 10, to introduce the fluid from the fluid introduction reservoir 21 through the inlet 14 into the microfluidic chip 10 due to a centrifugal force generated by rotation.

Figure 5:
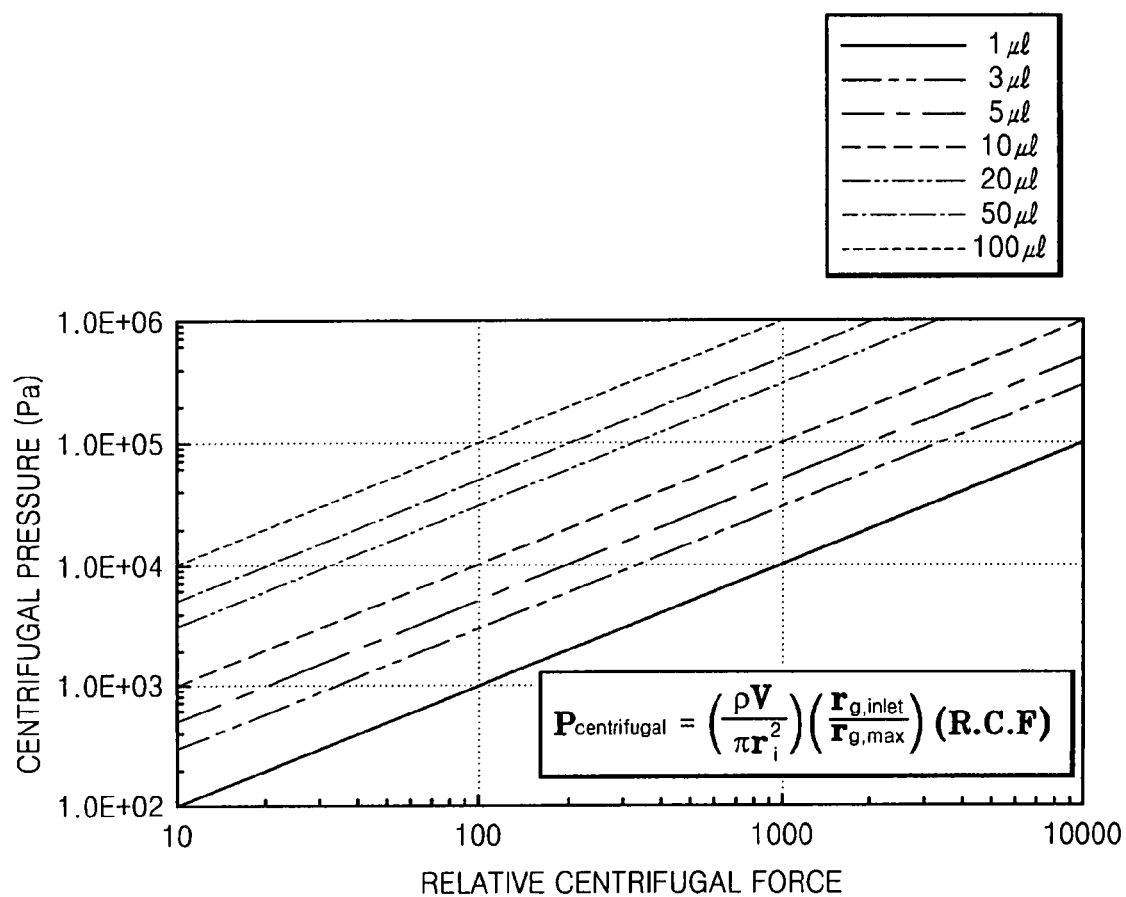
FIG. 5 is a graph illustrating a relationship between a centrifugal force and a centrifugal pressure according to the volume of a fluid in the exemplary fluid introduction apparatus of FIGS. 1A and 1B.

FIG. 5 is a graph illustrating a relationship between a centrifugal force and a centrifugal pressure according to the volume of a fluid in the exemplary fluid introduction apparatus of FIGS. 1A and 1B, in order to illustrate pressures generated by a predetermined volume of a fluid stored in the fluid introduction reservoir 21 under relative centrifugal forces ("RCFs"). The equation shown below and in the graph of FIG. 5 defines the relationship between the centrifugal force and the pressure.

$$P_{centrifugal} = \left(\frac{\rho V}{\pi r_i^2}\right)\left(\frac{r_{g,Inlet}}{r_{g,max}}\right)(R \cdot C \cdot F)$$

The variable $\rho$ denotes fluid density, V denotes fluid volume, $r_i$ denotes an inner radius of the exit of the introduction member, $r_{g,inlet}$ denotes a rotation radius of the inlet around a center of rotation, $r_{g,max}$ denotes a maximum rotation radius of a part of the tube furthest from the center of rotation and R.C.F denotes the relative centrifugal force.

For example, when the minimum pressure necessary to introduce a fluid into the inlet 14 of the microfluidic chip 10 is 3 Kpa, if there is a fluid of 10 μl in the fluid introduction reservoir 21, a centrifugal force of approximately 40 gravities (g) is applied to introduce the fluid, and if there is a fluid of 1 μl in the fluid introduction reservoir 21, a centrifugal force of approximately 300 g is applied to introduce the fluid.

Figure 6:
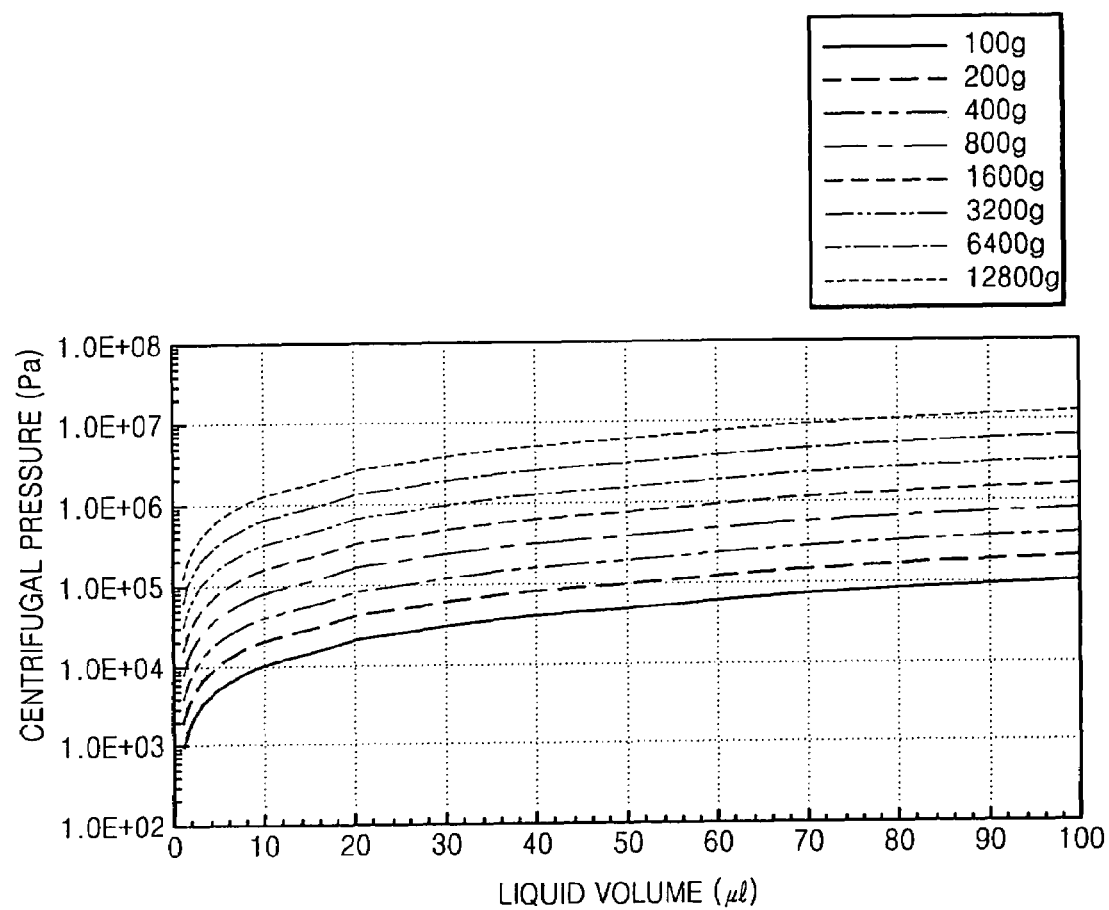
FIG. 6 is a graph illustrating a relationship between a fluid volume and a centrifugal pressure according to a relative centrifugal force applied to the exemplary fluid introduction apparatus of FIGS. 1A and 1B.

FIG. 6 is a graph illustrating a relationship between a fluid volume and a centrifugal pressure according to a relative centrifugal force applied to the exemplary fluid introduction apparatus of FIGS. 1A and 1B, illustrating the relationship of FIG. 5 from a different aspect by illustrating variations of the pressure as the volume of fluid in the fluid introduction reservoir 21 decreases under a constant centrifugal force. If the centrifugal force increases according to the volume of residual fluid in the fluid introduction reservoir 21 during fluid introduction into the microfluidic chip 10, the pressure can be maintained constant.

Figure 7:
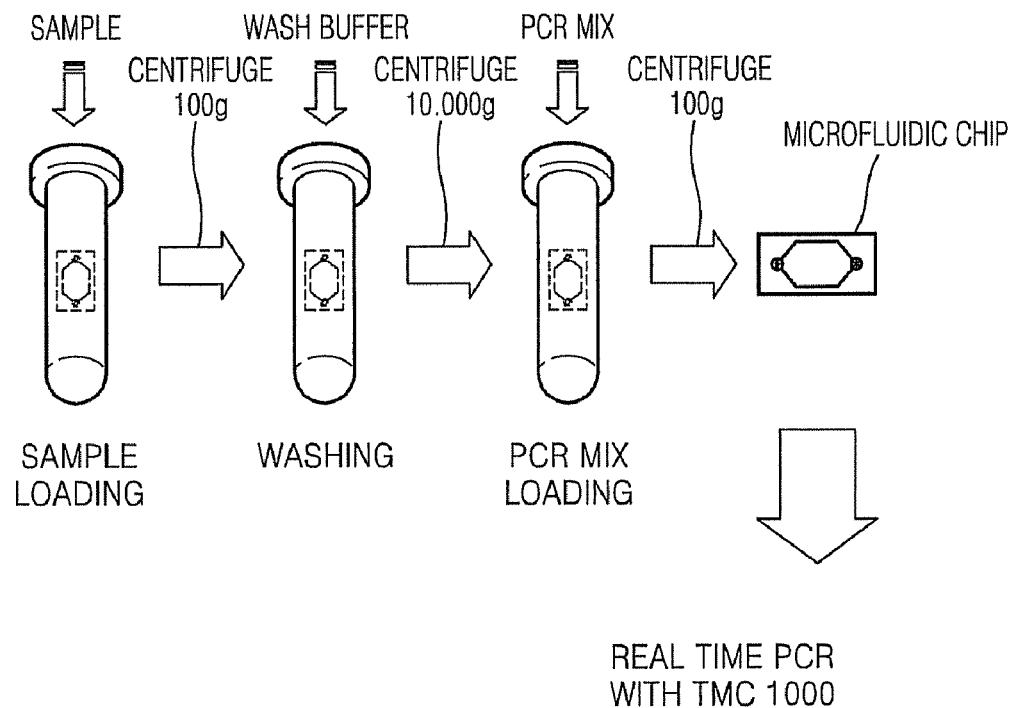
FIG. 7 illustrates an exemplary method of using an exemplary fluid introduction apparatus according to the present invention.
Figure 7:
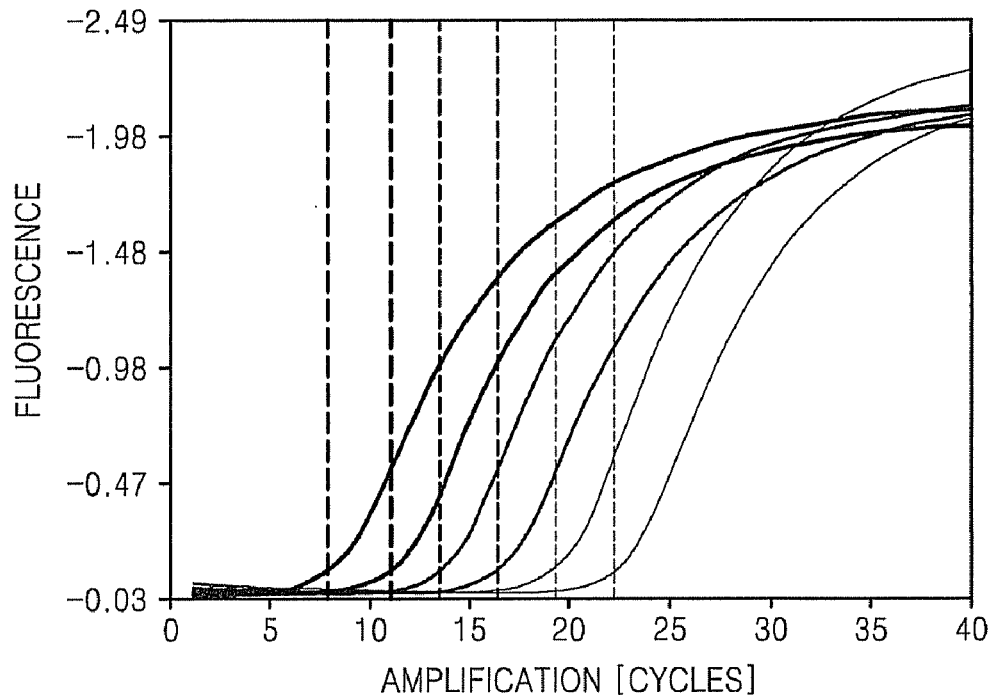

FIG. 7 illustrates an exemplary use of an exemplary fluid introduction apparatus according to an exemplary embodiment of the present invention for performing deoxyribonucleic acid ("DNA") concentration and amplification by means of a single microfluidic chip.

First, a microfluidic chip, including a chamber, and an inlet and an outlet in fluid communication with the chamber, and which may include a hydrophilic group on an inner wall of the chamber, is prepared on a substrate. The microfluidic chip is mounted in the exemplary fluid introduction apparatus according to the present invention. A sample containing DNA is introduced from the fluid introduction apparatus to the microfluidic chip via the inlet using a weak centrifugal force. Here, the DNA is bound in the chamber and the rest of the sample is discharged through the outlet.

Next, a buffer solution for washing is introduced into the microfluidic chip in the same manner as the sample was introduced as described above. In exemplary embodiments, during the washing, the microfluidic chip may be mounted in a new fluid introduction apparatus, or may be mounted in a new introduction member after the introduction member used in injecting the DNA containing sample is replaced with a new introduction member. In one exemplary embodiment, the washing buffer solution may be injected at a higher flow rate by using a higher centrifugal force than when the DNA containing sample is injected. Impurities in the microfluidic chip can be eliminated in this washing process.

Next, a polymerase chain reaction ("PCR") mixture is introduced into the microfluidic chip. In particular, to prevent contamination caused during the introduction of the PCR mixture, a new fluid introduction apparatus or a new introduction member may be used. A small volume of PCR mixture (4 μl) may be used and the introduced PCR mixture may remain in the microfluidic chip. The microfluidic chip, filled with the PCR mixture, is transported to a real-time PCR equipment to amplify the DNA.

Figure 8:
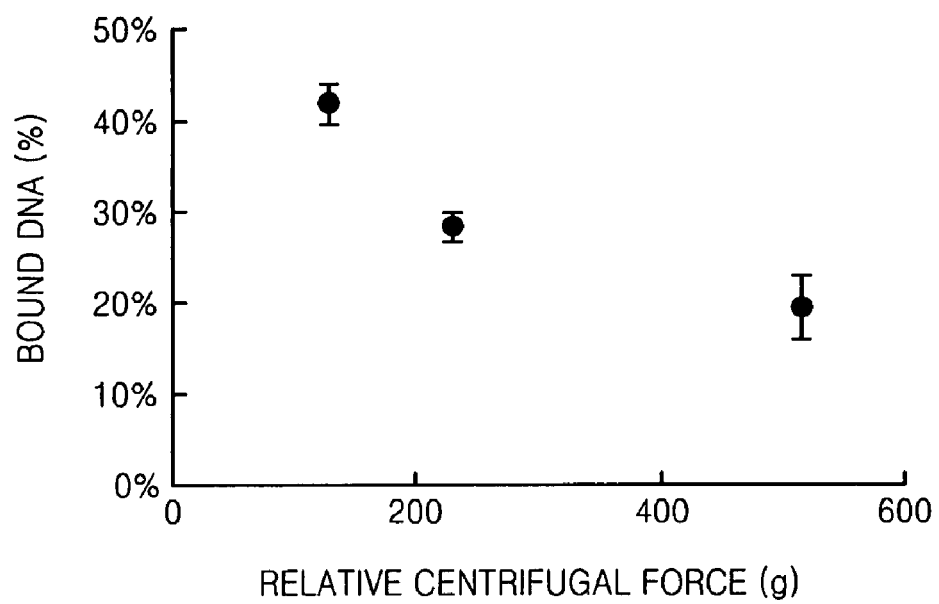
FIG. 8 is a graph illustrating a relationship between a centrifugal force and a percentage (%) of a deoxyribonucleic acid ("DNA")-containing sample that is bound when it is introduced using the exemplary fluid introduction apparatus of FIG. 7.

FIG. 8 is a graph illustrating a relationship between a centrifugal force and a percentage (%) of bound DNA when the DNA-containing sample is introduced using the exemplary fluid introduction apparatus of FIG. 7, illustrating the percentage (%), by volume, of the initially loaded DNA that is bound under each of the applied centrifugal forces. As the centrifugal force increases, the volume of DNA bound under the centrifugal force decreases because the flow rate in the microfluidic chip increases with the increase of the centrifugal force. The exemplary fluid introduction apparatus according to the present invention can easily control the flow rate by controlling the centrifugal force. Accordingly, in the above exemplary embodiment, DNA binding efficiency can be maximized by properly controlling the centrifugal force applied to the exemplary fluid introduction apparatus.

Figure 9:
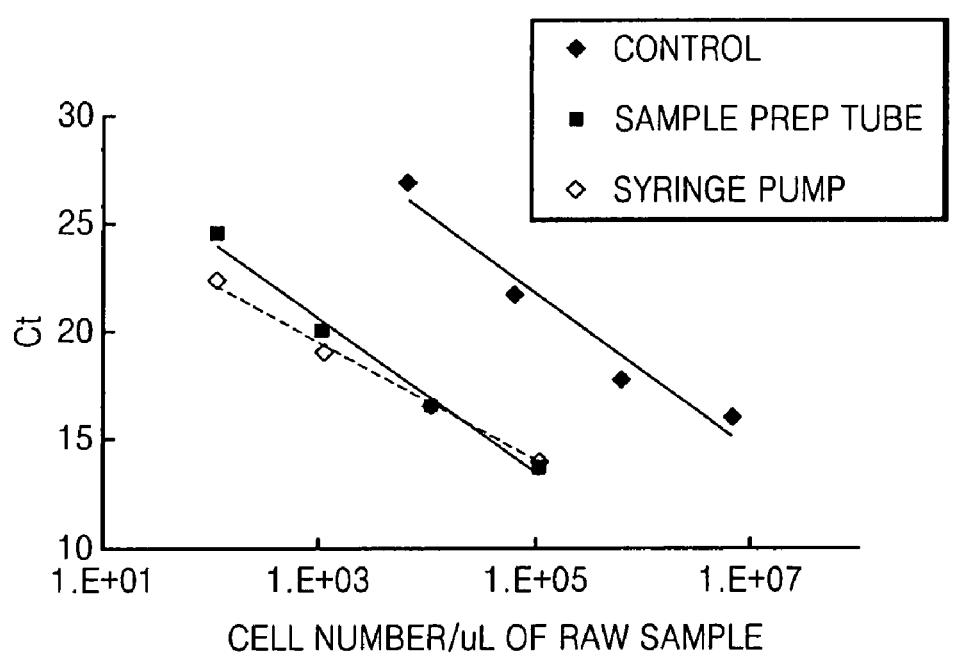
FIG. 9 is a graph illustrating a relationship between initial cell density and threshold cycle ("Ct") when the exemplary fluid introduction apparatus of FIG. 7 is used for DNA purification/concentration and real-time polymerase chain reaction ("PCR").

FIG. 9 is a graph illustrating initial cell density and threshold cycle ("Ct") when the exemplary fluid introduction apparatus of FIG. 7 is used for DNA purification/concentration and real time PCR. Referring to FIG. 9, the exemplary fluid introduction apparatus can offer results similar to those obtained by a conventional method that uses a syringe pump to inject a fluid.

The fluid introduction apparatus of the present invention can introduce a fluid with less effort in a shorter time than the conventional method, and can achieve almost the same work efficiency as that obtained from the conventional method.

As described above, the fluid introduction apparatus according to the present invention can introduce a fluid at a proper driving pressure into a microfluidic chip using a centrifugal force provided by a simple device. For example, the fluid introduction apparatus can provide an appropriate volume of fluid to the microfluidic chip including microchannels or microchambers using a microcentrifuge.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus introducing a fluid using a centrifugal force, the apparatus for comprising:
    an introduction member including a chip receiver and a fluid introduction reservoir, the chip receiver receiving a first part of a microfluidic chip, the first part including an inlet, the fluid introduction reservoir storing a fluid to be introduced to the microfluidic chip, the fluid introduction reservoir having an exit formed to correspond to the inlet of the microfluidic chip received in the chip receiver; and
    a support member supporting a second part of the microfluidic chip,
    wherein the introduction member, the microfluidic chip and the support member are separate members, the introduction member and the support member are combined with each other such that the first and second parts are received by the chip receiver and the support member, respectively, and the microfluidic chip is disposed between the introduction member and the support member, the apparatus is rotatable in a state where the introduction member is closer to a center of rotation than the microfluidic chip, and the fluid is introducible from the fluid introduction reservoir through the inlet into the microfluidic chip due to a centrifugal force generated by rotation.

2. The apparatus of claim 1, wherein the support member further includes a discharged fluid reservoir receiving a fluid discharged from an outlet of the microfluidic chip.

3. The apparatus of claim 1, wherein an outer surface of the chip receiver is attached to at least a portion of an outer surface of the microfluidic chip around the inlet of the microfluidic chip to prevent leakage of the fluid.

4. The apparatus of claim 1, wherein the support member is a tube-shaped container including a support which supports the microfluidic chip, and at least a portion of the introduction member is disposed within the tube-shaped container.

5. The apparatus of claim 1, wherein the support member is shaped to be received by a centrifuge.

6. A system for introducing a fluid by using a centrifugal force, the system comprising:
    an introduction member including a chip receiver and a fluid introduction reservoir, the chip receiver receiving a first part of a microfluidic chip, the first part including an inlet, the fluid introduction reservoir storing a fluid to be introduced to the microfluidic chip, the fluid introduction reservoir having an exit formed to correspond to the inlet of the microfluidic chip received in the chip receiver;
    a support member supporting a second part of the microfluidic chip, the microfluidic chip disposed between the support member and the introduction member wherein the introduction member, the microfluidic chip and the support member are separate members, the introduction member and the support member are combined with each other such that the first and second parts are received by the chip receiver and the support member, respectively, and the microfluidic chip is disposed between the introduction member and the support member; and
    a rotating device capable of rotating the support member and the introduction member in a state where the introduction member is closer to a center of rotation than the microfluidic chip, to introduce the fluid from the fluid introduction reservoir through the inlet into the microfluidic chip due to a centrifugal force generated by rotation.

7. The system of claim 6, wherein the support member further includes a discharged fluid reservoir receiving a fluid discharged from an outlet of the microfluidic chip.

8. The system of claim 6, wherein an outer surface of the chip receiver is attached to at least a portion of an outer surface of the microfluidic chip around the inlet of the microfluidic chip to prevent leakage of the fluid.

9. The system of claim 6, wherein the support member is a tube-shaped container including a support which supports the microfluidic chip, and at least a portion of the introduction member is disposed within the tube-shaped container.

10. The system of claim 6, wherein the rotating device is a centrifuge, and the support member is shaped to be received by the centrifuge.

11. A method of introducing a fluid into a microfluidic chip, the method comprising:
    preparing a fluid introduction apparatus, the apparatus comprising an introduction member including a chip receiver and a fluid introduction reservoir, the chip receiver receiving a first part of a microfluidic chip, the first part including an inlet, the fluid introduction reservoir having an exit formed to correspond to the inlet of the microfluidic chip received in the chip receiver, and a support member of the fluid introduction apparatus supporting a second part of the microfluidic chip, the introduction member, the microfluidic chip and the support member being separate members;
    combining the introduction member with the support member such that the first and second parts are received by the chip receiver and the support member, respectively, and the microfluidic chip is
    disposed in the fluid introduction apparatus between the introduction member and the support member;
    filling the fluid introduction reservoir with a fluid;
    rotating the fluid introduction apparatus in which the microfluidic chip is disposed by arranging the introduction member to be closer to a center of rotation than the microfluidic chips; and
    introducing the fluid from the fluid introduction reservoir into the microfluidic chip.

12. The method of claim 11, wherein the support member further includes a discharged fluid reservoir which receives a fluid discharged from an outlet of the microfluidic chip.

13. The method of claim 11, wherein an outer surface of the chip receiver is attached to at least a portion of an outer surface of the microfluidic chip around the inlet of the microfluidic chip to prevent leakage of the fluid.

14. The method of claim 11, wherein the support member is a tube-shaped container including a support which supports the microfluidic chip, and at least a portion of the introduction member is disposed within the tube-shaped container.

15. The method of claim 11, wherein the support member is shaped to be received by a centrifuge, and the centrifuge rotates the fluid introduction apparatus in which the microfluidic chip is disposed.

16. The method of claim 11, wherein the microfluidic chip farther comprises a chamber in which a biochemical reaction occurs, the inlet in fluid communication with the chamber and the outlet in fluid communication with the chamber, the outlet and the inlet disposed on opposite sides of the microfluidic chip.

17. The method of claim 11 further comprising repeating preparing the fluid introduction apparatus, filling the fluid introduction reservoir with a fluid, and rotating the fluid introduction apparatus for each type of fluid to be introduced into the microfluidic chip.

18. An apparatus for introducing a fluid into a microfluidic chip by using a centrifugal force, the apparatus comprising:
- an introduction member including a chip receiver and a fluid introduction reservoir, the chip receiver configured to receive a first part of the microfluidic chip, the fluid introduction reservoir configured to store a fluid, the fluid introduction reservoir having an exit leading to the chip receiver; and
- a support member configured to support a second part of the microfluidic chip, the support member shaped to be received by a rotating device,
- wherein the introduction member, the micro fluidic chip and the support member are separate members, the introduction member and the support member are combined with each other such that the first and second parts are received by the chip receiver and the support member, respectively, and the microfluidic chip is disposed between the introduction member and the support member.

19. The apparatus of claim 18,
- wherein an inlet of the microfluidic chip is in fluid communication with the exit of the fluid introduction reservoir, and fluid from the fluid introduction reservoir is introducible into the microfluidic chip using a centrifugal force generated by rotation of the apparatus.

20. The apparatus of claim 18, wherein the support member further includes a discharged fluid reservoir capable of receiving a fluid discharged from an outlet of the micro fluidic chip.

* * * * *